United States Patent
VanderKoy

(10) Patent No.: US 12,320,792 B2
(45) Date of Patent: Jun. 3, 2025

(54) BATTERY LIFE EXTENDER FOR INDOOR AIR QUALITY SENSOR

(71) Applicant: TRANE INTERNATIONAL INC., Davidson, NC (US)

(72) Inventor: Christopher C. VanderKoy, St. Paul, MN (US)

(73) Assignee: TRANE INTERNATIONAL INC., Davidson, NC (US)

( * ) Notice: Subject to any disclaimer, the term of this patent is extended or adjusted under 35 U.S.C. 154(b) by 929 days.

(21) Appl. No.: 17/139,724

(22) Filed: Dec. 31, 2020

(65) Prior Publication Data

US 2022/0205962 A1 Jun. 30, 2022

(51) Int. Cl.
| | |
|---|---|
| G01N 33/00 | (2006.01) |
| F24F 11/46 | (2018.01) |
| F24F 11/56 | (2018.01) |
| G05B 15/02 | (2006.01) |
| F24F 110/50 | (2018.01) |

(52) U.S. Cl.
CPC ............ *G01N 33/004* (2013.01); *F24F 11/46* (2018.01); *F24F 11/56* (2018.01); *G05B 15/02* (2013.01); *F24F 2110/50* (2018.01)

(58) Field of Classification Search
CPC .................................................. G01N 33/004
USPC ........................................................ 73/31.02
See application file for complete search history.

(56) References Cited

U.S. PATENT DOCUMENTS

| | | | |
|---|---|---|---|
| 10,767,879 B1 | 9/2020 | Burnett | |
| 2004/0253918 A1* | 12/2004 | Ezell | F24F 11/63 454/239 |
| 2015/0077737 A1 | 3/2015 | Belinsky et al. | |
| 2016/0041074 A1* | 2/2016 | Pliskin | G01N 15/0625 422/3 |
| 2016/0125730 A1 | 5/2016 | Sloo et al. | |
| 2017/0171941 A1* | 6/2017 | Steiner | H05B 47/105 |
| 2017/0343231 A1 | 11/2017 | Rumler et al. | |

(Continued)

FOREIGN PATENT DOCUMENTS

WO 2020/055872 A1 3/2020

OTHER PUBLICATIONS

Extended European Search Report issued in European Patent Application No. 21218152.3, May 30, 2022 (8 pages).

*Primary Examiner* — Walter L Lindsay, Jr.
*Assistant Examiner* — Philip T Fadul
(74) *Attorney, Agent, or Firm* — HSML P.C.

(57) ABSTRACT

A method extends battery life of a battery powered indoor air quality (IAQ) sensor that includes a IAQ detector, a radio, the battery, and a microcontroller with a memory and a processor. The method includes detecting IAQ at predetermined intervals to provide IAQ levels, and storing the IAQ levels and corresponding timing data in the memory. The method further includes determining an occupancy schedule based on IAQ level patterns and subdividing the occupancy schedule into a plurality of periods. The method further includes determining an occupancy status of each of the periods based on the IAQ levels. The method further includes operating the IAQ detector to sample at an active interval when the occupancy status is the occupied and at an inactive interval when the occupancy status is the unoccupied. The inactive interval is longer than the active interval. The IAQ detector can be, for example, a $CO_2$ detector or a VOC detector.

20 Claims, 3 Drawing Sheets

(56) References Cited

U.S. PATENT DOCUMENTS

2018/0017275 A1\* 1/2018 Merrill ..................... F24F 11/62
2019/0091700 A1\* 3/2019 Hilbig ....................... B03C 3/41
2021/0018884 A1\* 1/2021 Kupa ................... H05B 47/115

\* cited by examiner

BATTERY LIFE EXTENDER FOR INDOOR AIR QUALITY SENSOR

FIELD

This disclosure is generally directed to an indoor air quality ("IAQ") sensor for a heating, ventilation, air conditioning, and refrigeration ("HVACR") system. More particularly, this disclosure generally relates to methods for extending the battery life of an IAQ sensor that measures environmental conditions, such as carbon dioxide ("$CO_2$") levels and/or volatile organic compounds ("VOC") levels, in a controlled space.

BACKGROUND

An HVACR system utilize at least one sensors to monitor at least one environmental conditions of a controlled space. The controlled space can be a room, an office, a house, a building, a warehouse, a factory, a commercial building, and the like. The air sensors can measure IAQ parameters such as temperature, relative humidity, $CO_2$ levels, volatile organic compounds levels, and the like. Indoor air quality parameters measured by an IAQ detector may be referred to as an IAQ level. The HVACR system can be configured to wirelessly receive these sensor readings and to operate based on the IAQ levels detected. Some wireless sensors are powered by a battery.

SUMMARY

This disclosure is generally directed to an indoor air quality ("IAQ") sensor for a heating, ventilation, air conditioning, and refrigeration ("HVACR") system. More particularly, this disclosure generally relates to methods for extending the battery life of an IAQ sensor that measures environmental conditions, such as carbon dioxide ("$CO_2$") levels and/or volatile organic compounds ("VOC") levels, in a controlled space.

By including determining an occupancy schedule according to a history of IAQ levels in a controlled space, the IAQ sensors can detect IAQ levels at a longer interval when the controlled space is expected to be unoccupied and detect IA levels at a shorter interval when the controlled space is expected to be occupied. Increasing the sampling interval during some time periods can reduce the overall number of detection made and extend the battery life without sacrificing the reliability of the data. Accordingly, the battery life is of the IAQ sensor is extended without relying on a passive infrared ("PIR") module exclusively. Extending battery life by reducing sampling interval is effective with high energy consuming detectors, such as a $CO_2$ detector or a VOC detector. The high energy consuming detectors consume a substantially higher amount of energy to make detections compared to its energy consumption while idling.

According to one embodiment, a method for extending battery life of an IAQ sensor for a controlled space, includes: powering, using a battery, the IAQ sensor having a IAQ detector, a radio, the battery, and a microcontroller with a memory and a processor; detecting, using the IAQ detector, an IAQ at a predetermined interval to provide a plurality of IAQ levels; storing the IAQ levels in the memory; transmitting, using the radio, the IAQ levels to a remote controller for a HVACR system serving the controlled space; and adjusting a sampling interval for the IAQ detector according to the IAQ levels detected.

According to another embodiment, the IAQ detector is at least one of a $CO_2$ detector or a VOC detector, and IAQ level is at least one of a $CO_2$ level or a VOC level.

According to another embodiment, the IAQ detector is at least one of a CO2 detector or a VOC detector, and the IAQ level is at least one of a CO2 level or a VOC level.

According to another embodiment, the IAQ sensor further includes a real time clock ("RTC") providing corresponding timing data for the IAQ levels, and the corresponding time data are stored with the IAQ levels in the memory.

According to another embodiment, adjusting the sampling interval for the IAQ detector by: determining an occupancy schedule for the controlled space based on the IAQ levels and the corresponding timing data, the occupancy schedule subdivided into a plurality of periods, wherein the determining the occupancy schedule includes determining an occupancy status for each of the plurality of periods based on the IAQ levels and the corresponding timing data from a plurality of occupancy statuses, the plurality of occupancy statuses including occupied and unoccupied; operating the IAQ detector according to the occupancy schedule such that: the IAQ detector detects the IAQ at an active interval during each of the plurality of periods in which the occupancy status is the occupied, and the IAQ detector detects the IAQ at an inactive interval during each of the plurality of periods in which the occupancy status is the unoccupied, the inactive interval being longer than the active interval; and transmitting, using the radio, at least one IAQ level detected by the IAQ detector operating according to the occupancy schedule.

According to another embodiment, the method of further includes changing the occupancy status of one of the plurality of periods from the unoccupied to the occupied when the IAQ level detected during the one of the plurality of periods is above a first threshold value over a first predetermined number of detections; and changing the occupancy status of one of the plurality of periods from the occupied to the unoccupied when the IAQ level detected during the one of the plurality of periods is below a second threshold value over a second predetermined number of sampling.

According to another embodiment, adjusting the sampling interval biased towards over sampling.

According to another embodiment, adjusting the sampling interval biased towards over sampling by setting the first predetermined number to be smaller than the second predetermined number, or setting the first predetermined number, the inactive interval, the second predetermined number times, and the active interval so that a first product of the first predetermined number times the inactive interval is smaller than a second product of the second predetermined number times the active interval.

According to another embodiment, the method further includes detecting for the controlled space at least one of: a temperature level using a temperature detector, a humidity level using a humidity detector; or transmitting the temperature level, or the humidity level using the radio.

According to another embodiment, at least one of the $CO_2$ detector, the VOC detector, the temperature detector, or the humidity detector is a modular unit plugged into the IAQ sensor and is configured to be unplugged and removable from the IAQ sensor.

According to another embodiment, the occupancy schedule is determined using a machine learning algorithm included in the IAQ sensor, the occupancy status being determined by the machine learning algorithm, wherein the machine learning algorithm is configured to: read the IAQ levels and the corresponding timing data from the memory, and determine the occupancy status according to a pattern in the IAQ levels over time.

According to another embodiment, an IAQ sensor that measures IAQ levels in a controlled space, includes: a IAQ detector to detect IAQ at a sampling interval to provide a plurality of IAQ levels; a memory to store the IAQ level; a battery to power the IAQ sensor; a microcontroller configured to adjust a sampling interval for the IAQ detector according to the IAQ levels detected; and a radio to transmit at least one IAQ level detected by the IAQ detector to a remote controller for a HVACR system serving the controlled space.

According to another embodiment, the IAQ detector is at least one of a CO2 detector or a VOC detector, and the IAQ level is at least one of a CO2 level or a VOC level.

According to another embodiment, the IAQ sensor further includes a RTC providing corresponding timing data for the IAQ levels, and the corresponding time data are stored with the IAQ levels in the memory.

According to another embodiment, the microcontroller is further configured to adjust the sampling interval by: determining an occupancy schedule for the controlled space based on the IAQ levels and the corresponding timing data, the occupancy schedule subdivided into a plurality of periods, wherein the determining the occupancy schedule includes determining an occupancy status for each of the plurality of periods based on the $CO_2$ levels and the corresponding timing data from a plurality of occupancy statuses, the plurality of occupancy statuses including occupied and unoccupied; and operating the IAQ detector according to the occupancy schedule such that: the IAQ detector detects the IAQ at an active interval during each of the plurality of periods in which the occupancy status is the occupied, and the IAQ detector detects the IAQ at an inactive interval during each of the plurality of periods in which the occupancy status is the unoccupied, the inactive interval being longer than the active interval.

According to another embodiment, the microcontroller is further configured to adjust the sampling interval by: changing the occupancy status of one of the plurality of periods from the unoccupied to the occupied when the $CO_2$ level detected during the one of the plurality of periods is above a first threshold value over a first predetermined number of detections; and changing the occupancy status of one of the plurality of periods from the occupied to the unoccupied when the $CO_2$ level detected during the one of the plurality of periods is below a second threshold value over a second predetermined number of sampling.

According to another embodiment, the microcontroller is further configured to change the occupancy biased towards over sampling.

According to another embodiment, the microcontroller is further configured to change the occupancy biased towards over sampling by: setting the first predetermined number to be smaller than the second predetermined number, or setting the first predetermined number, the inactive interval, the second predetermined number times, and the active interval so that a first product of the first predetermined number times the inactive interval is smaller than a second product of the second predetermined number times the active interval.

According to another embodiment, the IAQ detector further includes at least one of a temperature detector to detect a plurality of temperature levels, and/or a humidity detector to detect a plurality of humidity levels in the controlled space; and the radio to transmit at least one of the temperature levels, and/or at least one of the humidity levels to the remote controller for the HVACR system serving the controlled space.

According to another embodiment, at least one of the $CO_2$ detector, the VOC detector, the temperature detector, or the humidity detector is a modular unit that can be plugged into the IAQ sensor and configured to be unplugged and removable from the IAQ sensor.

According to another embodiment, the occupancy schedule is determined using a machine learning algorithm included in the IAQ sensor, the occupancy status being determined by the machine learning algorithm, wherein the machine learning algorithm is configured to: read the IAQ levels and the corresponding timing data from the memory, and determine the occupancy status according to a pattern in the IAQ levels over time.

BRIEF DESCRIPTION OF THE DRAWINGS

References are made to the accompanying drawings that form a part of this disclosure, and which illustrate embodiments in which the systems and methods described in this Specification can be practiced.

Like reference numbers represent like parts throughout.

DETAILED DESCRIPTION

A heating, ventilation, air conditioning, and refrigeration ("HVACR") system can utilize at least one wireless an indoor air quality ("IAQ") sensor(s) to monitor the environmental conditions of a controlled space (e.g., temperature, relative humidity, carbon dioxide ("$CO_2$"), volatile organic compound(s) ("VOC"), and the like). The controlled space can be, for example, a room, an office, a house, a building, a warehouse, a factory, a commercial building, and the like. The HVACR system can be configured to wirelessly receive the sensor readings or IAQ levels from the IAQ sensor(s) and to operate the HVACR system based on the IAQ levels detected.

Many IAQ sensors are battery powered. Replacing batteries can increase the material and the labor cost of operating the HVACR system. Sensors consume more energy when sampling or detecting the IAQ levels. Conventionally, passive infrared ("PIR") modules have been integrated into IAQ sensors to determine the occupancy of a controlled space. A conventional IAQ sensor can increase the sampling interval when the controlled space is deemed unoccupied according to the PIR module and decrease the sampling interval when the controlled space is deemed occupied according to the PIR module. However, the effectiveness of a modular IAQ sensor with an integrated PIR module depends on the location and/or configuration of a host device on which the IAQ sensor and the PIR sensor are installed. This is, for example, because PIR sensors are more suitable to be installed on the ceiling, while a $CO_2$ detector can be more suitable to be installed closer to the floor. For example, if a host device is installed near the floor, the PIR module in the IAQ sensor can be less effective in detecting the occupancy of the controlled space. Accordingly, the PIR module is less effective in extending the battery life of the IAQ sensor. If a host device is installed on the ceiling, the PIR is more effective in detecting the occupancy of the room. However, the $CO_2$ detector in the IAQ sensor can be less accurate when installed on the ceiling. Furthermore, the incorporation of the PIR module into the IAQ sensor can increase the complexity, the energy consumption, and the cost of the IAQ sensor.

Embodiments disclosed herein are directed to IAQ sensors, HVACR systems including IAQ sensor(s), methods for extending the battery life of an IAQ sensor. Embodiment described herein are configured to utilize IAQ levels of an IAQ sensor to reduce the power consumption of the IAQ sensor. In some embodiments, the IAQ levels, such as $CO_2$ levels or VOC levels, are used to determine an occupancy of a controlled space and to utilize longer sampling intervals during times with lower or no occupancy. In other embodiments, the IAQ levels, such as CO2 levels or VOC levels, are used to check against at least one threshold value(s) to increase or decrease the sampling interval.

Figure 1:
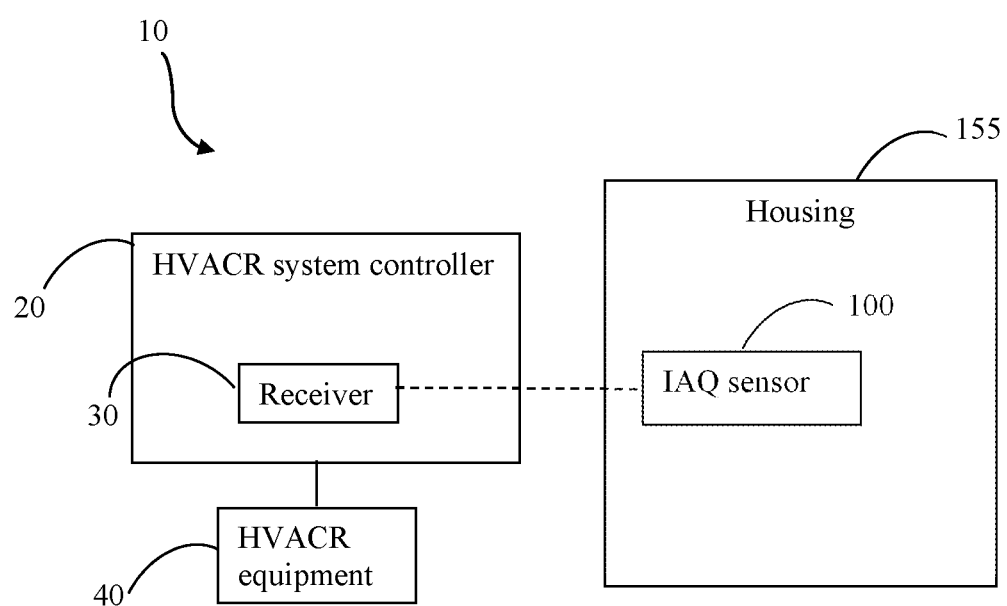
FIG. 1 is a schematic diagram of an HVACR system, according to one embodiment.

FIG. 1 is a schematic diagram of an HVACR system 10, according to one embodiment. The HVACR system 10 includes a IAQ sensor 100. The IAQ sensor 100 provides IAQ data to be used by the HVACR system 10 for a controlled space. The IAQ data include the IAQ levels detected by each of the IAQ detector(s) of the IAQ sensor 100. For example, the IAQ levels can include at least one of a $CO_2$ level, a VOC level, a temperature level, a relative humidity level, or the like. The IAQ sensor 100 can further include a housing 155. According to one embodiment, all the components of the IAQ sensor 100 are disposed in the housing 155. According to another embodiment, one or more component(s) of the IAQ sensor 100 is disposed in the housing 155. According to yet another embodiment, the IAQ sensor 100 can be fully or partially contained in at least one housing(s) 155 that each contains at least one components of the IAQ sensor 100.

The HVACR system 10 includes a HVACR system controller 20. According to one embodiment, the IAQ sensor 100 transmits IAQ levels to an HVACR system controller 20. The IAQ sensor 100 includes a radio. The radio can transmit the IAQ levels. In an embodiment, the radio includes a transmitter component to transmit the IAQ levels. The HVACR system controller 10 can include a receiver 30 that receives the IAQ levels transmitted from the IAQ sensor 100. In an embodiment, the receiver 30 can be a radio wave receiver. The HVACR system 10 can also include HVACR equipment 40 such as temperature and/or humidity regulating equipment, air quality regulating equipment, IAQ data collecting and/or processing equipment, and the like. According to one embodiment, the HVACR equipment 40 can be a refrigeration circuit (not shown). The refrigeration circuit includes a compressor, an expander, an evaporator, and a condenser. The HVACR system 10 can include at least one ventilation device(s) (e.g., an air handler, a fan, a blower, or the like) (not shown). The HVACR system 10 can be capable of supplying external air (e.g., air from outside the controlled space, ambient air, and the like) to the controlled space to ventilate the controlled space. The HVACR system 10 can have a recirculation mode in which a majority of the air conditioned by the HVACR system 10 and supplied to the controlled space is indoor air from the controlled space. The HVACR system 10 can also include a ventilation mode that exhausts the indoor air and supplies a majority of external air into the controlled space.

The HVACR system controller 20 can operate the HVACR system 10 in the recirculation mode when the current IAQ level from the IAQ sensor 100 is below a predetermined value. If the IAQ level(s) from the IAQ sensor 100 is above the predetermined value, the HVACR system controller can operate the HVACR system 10 in the ventilating mode in order to lower the IAQ level of the controlled space. For another example, temperature and/or humidity ("T/RH") level(s) can be transmitted directly to the HVACR system controller 20 for operating the heating/cooling of the HVACR system 10. The HVACR system controller 20 can use the T/RH level to operate the heating and cooling components of the HVACR system 10 (e.g., the components of the refrigeration circuit, a heater of the HVACR system, and the like). According to another embodiment, the IAQ level(s) can be transmitted from the IAQ sensor 100 to an HVACR system controller 20 acting as a data repository, such as a central controller, a remote controller, or a server. A controller for a particular device of the HVACR system 10 can acquire data needed for its operation from the central controller. The IAQ level can be a $CO_2$ level, a VOC level, or the like.

According to yet another embodiment, the IAQ sensor 100 can be a modular device. The modular IAQ sensor can plug into a host device, expanding the functionalities of the host device to include IAQ detecting functionalities. For example, the host device can be an IAQ monitor. Without exclusively relying on a PIR sensor to determine occupancy of the controlled space, the IAQ sensor 100 can be added to a host device without the limitations of PIR sensors.

Figure 2:
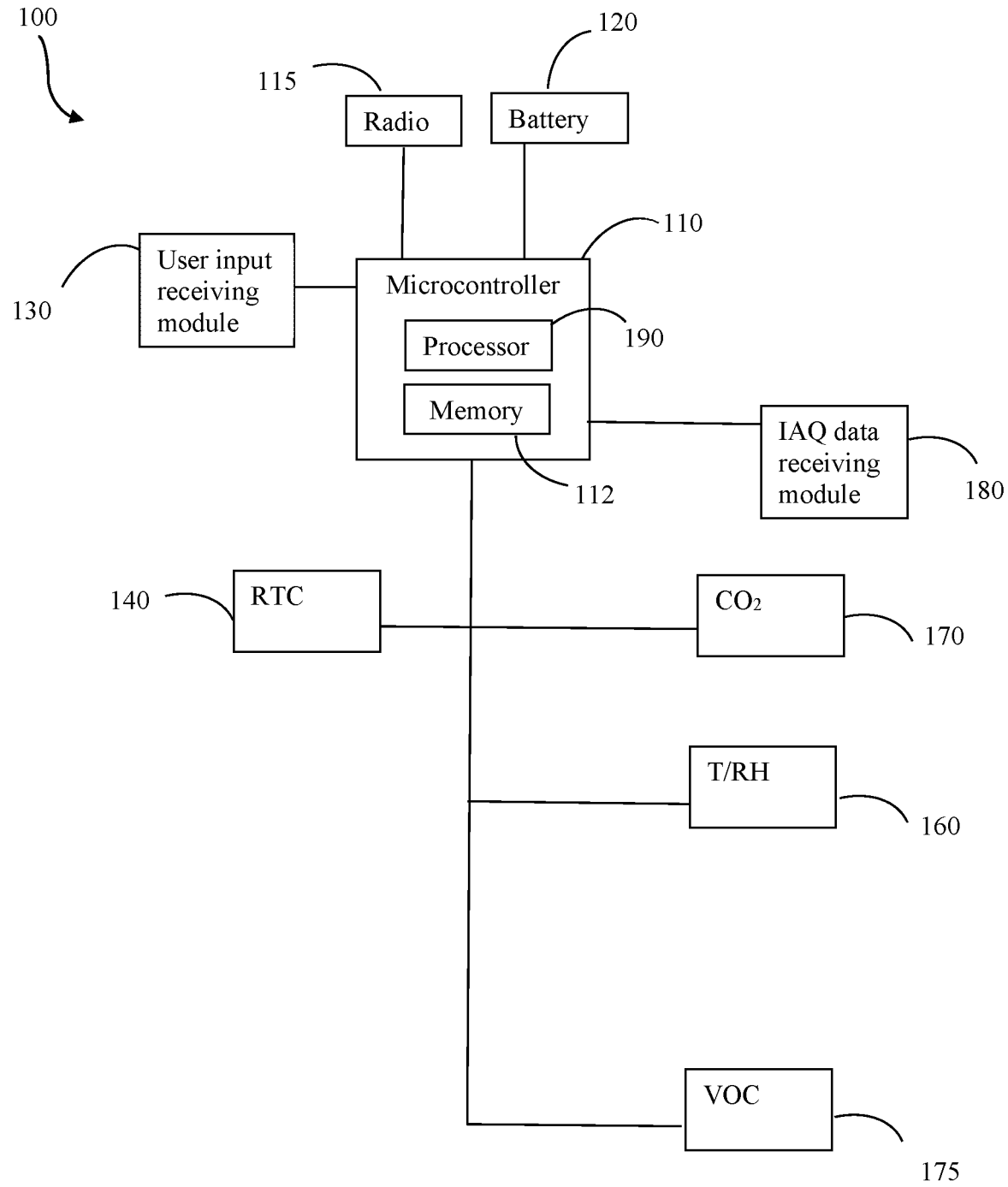
FIG. 2 is a schematic diagram of an IAQ sensor that measures IAQ levels, according to one embodiment.

FIG. 2 is a schematic diagram of the IAQ sensor 100 that measures $CO_2$ levels, according to one embodiment. As shown in FIG. 2, the IAQ sensor 100 includes a microcontroller 110, a radio 115, a battery 120, and at least one IAQ detector(s) (e.g., a $CO_2$ detector 170, a VOC detector 175, or the like). The IAQ sensor 100 can further include a real time clock ("RTC") 140. The microcontroller 110 includes a processor 190 and a memory 112. The processor 112 is configured to access the memory 190. For example, the microcontroller 110 operates by its processor 112 reading and operating according to instructions stored on the memory 190.

According to one embodiment, the microcontroller 110, the radio 115, the battery 120, the RTC 140, and the IAQ detector(s) are connected on an integrated circuit board of the IAQ sensor 100. In an embodiment, at least one of the radio 115, battery 120, RTC 140, VOC detector 175, or $CO_2$ detector 170 can be a separate component non-wirelessly connected (e.g., wired, soldered, plugged into, and the like) to the microcontroller 110. For example, said component(s) may be a module that is plugged into the IAQ sensor 100 (e.g., plugged into the microcontroller 110) and is configured to be unplugged and non-destructively removed from the IAQ sensor 100.

The IAQ sensor 100 includes at least one of IAQ detectors. For example, the IAQ detectors can be, but are not limited to, the $CO_2$ detector 170, a VOC detector 175, a temperature and/or relative humidity ("T/RH") detector 160, and the like.

IAQ levels can be stored and transmitted as IAQ data measured by at least one IAQ detectors of a controlled space. For example, the IAQ data can be $CO_2$ levels, VOC levels, temperature, relative humidity, and the like. The controlled space can be a room, a house, an office area, a building, a warehouse, a factory, a commercial building, and the like.

The processor 112 of the microcontroller 110 can read and write data from the memory 190. According to one embodiment, the microcontroller 110 reads and writes IAQ levels detected by the IAQ detector(s) into a history buffer on the memory 190. The microcontroller 110 can read and operate on the IAQ levels acquired from the memory 190 according to a preprogrammed algorithm. According to another embodiment, the microcontroller 110 can read and operate on the IAQ levels according to a machine learning algorithm. The machine learning algorithm can be trained and/or updated by the IAQ levels obtained by the IAQ sensor 100.

The microcontroller 110 can further include other components for the IAQ detectors. For example, the microcontroller 110 can include the radio 115 and operate the radio 115 to wirelessly transmit IAQ data to a remote device, such as a database, a server, a controller, and the like. According to an embodiment, the radio 115 can be any suitable transmitter(s) and/or receiver(s). For example, the radio 115 can include a radiowave transmitter, a radiowave receiver, or both. According to yet another embodiment, the radio 115 and a IAQ data receiving module 180 can share the same transmitter(s) and/or receiver(s). The microcontroller 110 can receive user input through a user input receiving module 130 of the IAQ sensor 100. For example, the user input receiving module 130 can be a capacitive touch screen and/or tactile switch(es) accessible to the user. The microcontroller 110 can be configured to control a sampling interval of at least one the IAQ detector(s). The microcontroller 110 can instruct a user display for showing a message to the user. According to an embodiment, the microcontroller 110 can non-wirelessly connect (e.g., wired, soldered, plugged into, and the like) to and be configured to control other components for the IAQ detectors via electrical signals.

The memory 190 stores IAQ data. The memory 190 can be at least one flash memory integrated onto the circuit board shared with the processor 112 of the microcontroller 110. According to one embodiment, the memory 190 can include multiple memory portions non-wirelessly connected to the processor 112. For example, the memory 190 can include a first memory portion for storing the IAQ data a second memory portion for storing the algorithm(s) for operating the IAQ sensor 100 as discussed below. The IAQ data can be the IAQ levels detected by the IAQ sensor 100. The memory 109 can include a history of IAQ levels for the microcontroller 110 to determine the occupancy of the controlled space, assign occupancy status, determine an occupancy schedule, and update the occupancy schedule. According to an embodiment, the memory 190 can be at least one serial flash memory.

Data stored in the memory 190 can include the IAQ level(s) acquired by the IAQ sensor, such as $CO_2$ levels detected by the $CO_2$ detector 170, timing data from the RTC 140, T/RH levels detected by the T/RH detector 160, VOC levels detected by the VOC detector 175, an external IAQ data input (e.g., temperature input) from an IAQ data receiving module 180, and the like. The memory 190 can store algorithm(s) for operating the IAQ sensor and/or for operating the IAQ detectors. The algorithm(s) can be read and performed by the processor 112 of the microcontroller 110. The algorithm can be preprogrammed instructions for operating certain components of the IAQ sensor 100. For example, the algorithm can include programs for controlling the $CO_2$ detector 170 or the VOC detector 175 in order to detect $CO_2$ levels or VOC levels at a predetermined interval during a powerup period. For example, the microcontroller 110 can perform the program for controlling the sampling interval of the $CO_2$ detector 170 or VOC detector 175 so that the $CO_2$ detector 170 or the VOC detector 175 detects the $CO_2$ level or the VOC level in the controlled space every 5 minutes, 10 minutes, or 15 minutes. The algorithm can include programs for saving the $CO_2$ levels or the VOC levels acquired from the $CO_2$ detector 170 or the VOC detector 175 in the memory 190. The algorithm can also include programs for transmitting acquired IAQ levels using the radio 115.

The radio 115 is a module on a circuit board of the IAQ sensor 100 for sending and/or receiving data between the IAQ sensor 100 and other remote devices. The other remote devices can be a controller of the HVACR system, a controller for a particular HVACR device, a server, a computer, and the like. The radio 115 sends and/or receives electrical signals wirelessly. According to one embodiment, the radio 115 transmits IAQ data after each detecting by the detector. For example, the radio 115 can be configured to transmit the $CO_2$ levels after each sampling of the $CO_2$ detector 170. For example, the radio 115 can be configured to transmit the VOC levels after each sampling of the VOC detector 175.

The IAQ sensor can include a battery 120. The battery 120 provides electrical power to the IAQ sensor 100 and its components, such as the radio 115, the microcontroller 110, the $CO_2$ detector 170, the RTC 140, the temperature and/or relative humidity detector 160, the VOC detector 175, the memory 190, and the like. In one embodiment, the battery 120 provides all the power for the IAQ sensor 100. According to another embodiment, the battery 120 is a primary source of power for the IAQ sensor 100, where there may be other power sources.

The components of the IAQ sensor 100 draw electrical power from the battery 120. For example, the $CO_2$ detector 170 draws electrical power from the battery 120 and consumes electrical power in detecting the $CO_2$ level of the controlled space. The $CO_2$ detector 170 consumes electrical power to transmit the detected $CO_2$ level to the microcontroller 110. The microcontroller 110 consumes power to write the $CO_2$ levels into the memory 190. The microcontroller 110 and the radio 115 further consumes power to transmit the detected $CO_2$ level to a remote device. According to one embodiment, the battery 190 can be at least one battery units.

The RTC 140 is a microcontroller component that provides timing data to the IAQ sensor 100. In some embodiments, the RTC 140 may be integrated into the microcontroller 110 along with the processor 112 and/or the memory 190. According to one embodiment, the RTC 140 tracks and provides timing data relative to a starting point in time. For example, the relative time can be a number of seconds since the IAQ sensor was powered on. According to another embodiment, the RTC 140 tracks and provides real-world time. For example, the RTC 140 can track and provide the hours, the minute, the second, the month, the date, and the year.

The $CO_2$ detector 170 measures the $CO_2$ in the controlled space and provides the detected $CO_2$ level to the microcontroller 110 of the IAQ sensor 100. The $CO_2$ detector 170 can be configured to make detections at a predetermined interval. For example, the $CO_2$ detector 170 can be configured to make a detection once every 5 minutes, 10 minutes, or 15 minutes. The $CO_2$ detector 170 draws power from the battery 120 and consumes an amount of power generally proportional to the number of detections. For example, if the $CO_2$ detector 170 is detecting at a 5-minute interval over an 8-hour period, the $CO_2$ detector 170 would have consumed about twice as much energy as the $CO_2$ detector 170 would have consumed if the $CO_2$ detector 170 were detecting at a 10-minute interval over the same 8 hour period. According to an embodiment, energy required for detecting, processing, transmitting, and saving IAQ level can be a significant portion of all the energy consumed by the IAQ sensor 100. Accordingly, reducing the sampling number while providing IAQ data that accurately reflects the pattern of IAQ level in a controlled space can extend the battery life of the IAQ sensor.

According to an embodiment, the $CO_2$ detector 170 can be a modular device plugged into the IAQ sensor 100 and is configured to be non-destructively unplugged from the IAQ sensor 100. According to another embodiment, the $CO_2$ detector 170 can be one of the IAQ detectors of the IAQ sensor 100 that measures IAQ parameter levels of a controlled space.

In an embodiment, the $CO_2$ detector 170 is a microcontroller component that detects $CO_2$ levels in a controlled space. For example, the $CO_2$ detector 170 can be detecting $CO_2$ levels using a photoacoustic or a non-dispersive infrared ("NDIR") method. A $CO_2$ detector 170 can be a module that communicates with rest of the microcontroller 110 over a standardized medium, such as Universal Asynchronous Receiver/Transmitter ("UART"), or a communication protocol, such as Inter-Integrated Circuit ("I2C"). In an embodiment, the $CO_2$ detector 170 can include a microcontroller, an infrared ("IR") emitter, an IR detector, and an optical box to reflect the IR energy many times across a certain sample of air. The IR energy is of a predetermined wavelength that is absorbed by $CO_2$ molecules in the sample of air. After an IR energy is emitted by the emitter, the IR energy is reflected within the optical box for a predetermined time to crease an effective length of a path traveled by the IR energy. Then, the IR energy is detected by the IR detector. The higher level of $CO_2$ presented in the sample of air, the more IR energy is absorbed by the sample of air and the less IR energy is detected by the IR detection. The loss of IR energy is correlated to a concentration of $CO_2$ level within a sample of air. The $CO_2$ level is then communicated to another microcontroller component, such as the microcontroller 110. The IR energy can be a continues beam of energy, a pulse, or the like. Generating the IR energy is an energy intensive process.

The microcontroller 110 can connect to more than one detector such that making the IAQ sensor a multi-sensor. According to one embodiment, the microcontroller 110 can non-wirelessly connect (e.g., wired, soldered, plugged into, and the like) to more than one detectors such that making the IAQ sensor a multi-sensor. For example, the microcontroller 110 can connect to a $CO_2$ detector 170 and a T/RH detector 160. For example, the microcontroller 110 can further connect to a VOC detector 175. According to another embodiment, the microcontroller 110 connects its components, such as the $CO_2$ detector 170, using a communication protocol. For example, the communication protocol can be I2C.

The T/RH detector 160 can be further included in the IAQ sensor 100. The T/RH detector 160 can detect the temperature and/or the relative humidity levels of the controlled space and provide the temperature and/or the relative humidity levels to the IAQ sensor 100. The T/RH detector 160 is configured to be detecting the temperature and/or the relative humidity levels at a predetermined interval. For example, the T/RH detector 160 can be configured to make detection once every 5 minutes, 10 minutes, or 15 minutes. According to one embodiment, the T/RH detector 160 draws power from the IAQ sensor 100 and consumes an amount of power generally proportional to the number of detection. For example, if the T/RH detector 160 is detecting at a 5-minute interval over an 8-hour period, the T/RH detector 160 would have consumed about twice as much as energy as the T/RH detector 160 would have consumed if the T/RH detector 160 were detecting at a 10-minute interval over the same 8-hour period. According to another embodiment, the T/RH detector 160 can be a modular device that can be plugged or unplugged, non-destructively, from the IAQ sensor 100. According to another embodiment, the T/RH detector 160 can be one of the IAQ detectors of the IAQ sensor 100 that measures IAQ levels of the controlled space.

A volatile organic compounds ("VOC") detector 175 can be included in the IAQ sensor 100. The VOC detector 175 can detect the VOC levels of the controlled space and provide VOC levels to the IAQ sensor 100. The VOC detector 175 is configured to be detecting VOC levels at a predetermined interval. For example, the VOC detector 175 can be configured to be detect VOC levels once every 5 minutes, 10 minutes, or 15 minutes. According to one embodiment, the VOC detector 175 draws power from the IAQ sensor 100 and consumes an amount of power generally proportional to the number of sampling. For example, if the VOC detector 175 is detecting at a 5-minute interval over an 8-hour period, the VOC detector 175 would have consumed about twice as much as energy as the VOC detector 175 would have consumed if the VOC detector 175 were detecting at a 10-minute interval over the same 8-hour period. According to another embodiment, the VOC detector 175 can be a modular device that can be plugged or unplugged, non-destructively, from the IAQ sensor 100. According to another embodiment, the VOC detector 175 can be one of the IAQ detectors of the IAQ sensor 100 that measures IAQ levels of a controlled space through sampling.

In an embodiment, the VOC detector 175 is a microcontroller component that detects VOC levels in a controlled space. The VOC detector 175 can be a VOC detector that measure a VOC level or an accumulative VOC level in a sample of air. The total VOC level can include an accumulative concentration or level of at least one of organic compounds such as: methane, methanol, ethane, ethanol, benzene, ethylene glycol, formaldehyde, toluene, xylene, butadiene, or the like. The VOC detector 175 can be detecting VOC levels using a resistor of which the resistance changes corresponding to the VOC level in the sample of air. According to an embodiment, the resistor is made from a metal oxide material that is heated when making a detection or measurement of the VOC level in the sample of air. Heating the resistor is an energy intensive process.

It will be appreciated that the housing 155 can contain some or all the components of the IAQ sensor 100. For example, the housing 155 can contain the microcontroller 110, the memory 190, and the processor 112. Other components of the IAQ sensor 100, for example, the VOC detector 175, or the user input receiving model 130 can be positioned outside the housing 155 and connected to the components of the IAQ sensor 100 within the housing 155 through a wired connection. According to yet another embodiment, the user input receiving module 130 can be connected non-wirelessly to the components of the IAQ sensor 100 within the housing 155. For example, the microcontroller 110 can be configured to operate the components of the IAQ sensor 100, within or outside the housing 155. According to another embodiment, the components of the IAQ sensor 100 can be fully or partially contained in one or more housings 155 each containing one or more component(s) of the IAQ sensor 100. The IAQ sensor 100 can receive input from external devices through a receiving module. According to one embodiment, the receiving modules can be a user input receiving module 130 that receives input from a user. For example, the user input receiving module 130 can be at least one capacitive touch sensor(s). For another example, the user input receiving module 130 can be at least one tactile buttons. According to another embodiment, a receiving module can be an IAQ data receiving module 180 receives IAQ data from external sources. For example, an external source may be temperature data from a database. The temperature data can be temperature data of the controlled space, another controlled space, the outside environment, or the like.

Figure 3:
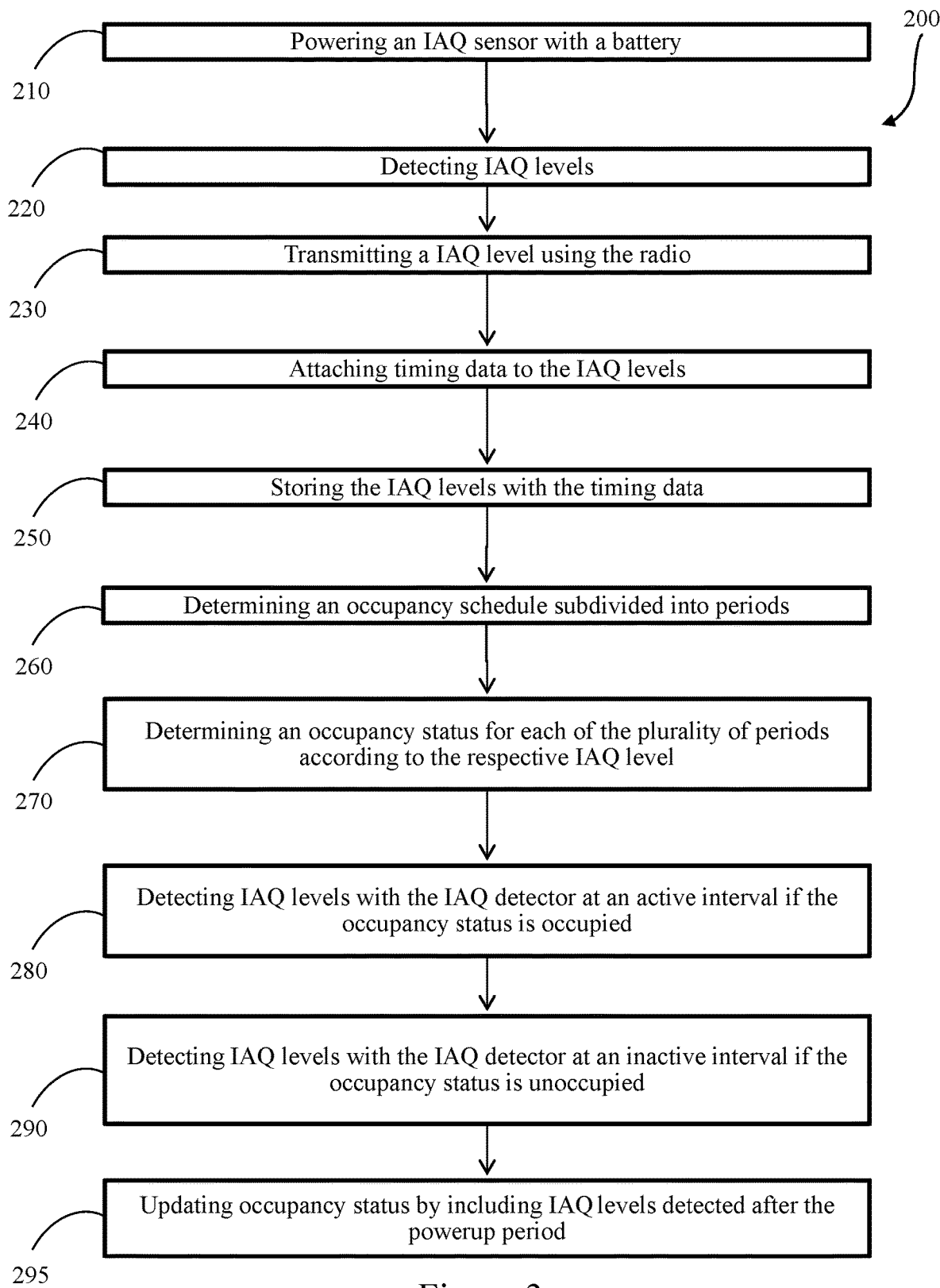
FIG. 3 is a block diagram of a method for extending battery life of an IAQ sensor that measures IAQ levels of a controlled space, according to one embodiment.

FIG. 3 is a block diagram of a method 200 for extending battery life of an IAQ sensor that measures IAQ levels and other IAQ levels of a controlled space, according to one embodiment. As shown in FIG. 3, the method 200 includes powering an IAQ sensor with a battery 210; detecting IAQ levels 220; transmitting a IAQ level using a radio 230; attaching timing data to the IAQ levels 240; storing the IAQ levels with the timing data 250; determining an occupancy schedule subdivided into a plurality of periods 260; determining an occupancy status for each of the plurality of periods according to the IAQ levels 270; detecting IAQ levels with the IAQ detector at an active interval if the occupancy status is occupied 280; detecting IAQ levels with the IAQ detector at an inactive interval if the occupancy status is unoccupied 290; and updating occupancy status by including IAQ levels detected after the powerup period 295. According to an embodiment, the VOC detector can be at least one of a $CO_2$ detector, a VOC detector, or the like.

The method 200 includes powering an IAQ sensor with a battery 210, particularly powering the IAQ sensor having a $CO_2$ detector, a VOC detector, a radio, an RTC, a memory, a microcontroller, and a battery powering the IAQ sensor. The IAQ sensor can be a wireless IAQ sensor that relies on battery power to operate the components of the IAQ sensor. According to one embodiment, the $CO_2$ detector, the radio, the RTC, the memory, the microcontroller, the battery, or the IAQ sensor can respectively be the $CO_2$ detector 170, the VOC detector 175, the radio 115, the RTC 140, the memory 190, the microcontroller 110, the battery 120, or the IAQ sensor 100 as shown and described in FIGS. 1 and 2.

The method 200 further includes detecting IAQ levels 220, particularly detecting IAQ levels with the IAQ detector at a predetermined interval. The predetermined interval can be a default detection interval preprogrammed into the IAQ detector by the manufacturer. The predetermined interval is short so that a sufficient amount of IAQ levels is collected to accurately reflect a pattern of IAQ levels in the controlled space over a time period. The IAQ detector consumes a relatively higher amount of energy when detecting IAQ levels at a short sampling interval. According to an embodiment, the time period can be a powerup period when the IAQ sensor is sampling at the short predetermined interval. According to another embodiment, the microcontroller of the IAQ sensor clears its history buffer upon powering up. The history buffer cleared can contain patterns of IAQ levels or IAQ levels with timing data no longer applicable to the controlled space. The history buffer can locate in the memory of the IAQ sensor. According to an embodiment, the powerup period can be a week or a multiple of a week. According to another embodiment, an algorithm performed by a processor of the microcontroller can determine the powerup period once the microcontroller detects a repeating pattern of the IAQ levels.

The method 200 further includes transmitting IAQ levels using the radio 230. According to one embodiment, the microcontroller of the IAQ sensor operates the radio to transmit the IAQ levels after each detection by the IAQ detector.

The method 200 further includes attaching timing data to the IAQ level 240, particularly attaching timing data from the RTC to the IAQ level detected. According to one embodiment, the microcontroller of the IAQ sensor acquires timing data from the RTC for each of the IAQ levels detected. The microcontroller associates the timing data with the respective IAQ level and writes the IAQ level with the timing data in the memory. According to an embodiment, the IAQ level with the timing data are located in a history buffer of the memory. The IAQ levels are attached to the respective timing data so that a dataset of the IAQ level over time can be constructed. According to one embodiment, the microcontroller can use the dataset to recognize a pattern of IAQ level within the controlled space over time. According to another embodiment, the microcontroller can use the dataset to recognize at least one threshold value(s) of the IAQ level within the controlled space over time. The threshold value(s) can be used to determine the controlled space is occupied when the IAQ level detected is above a threshold value, the controlled space is unoccupied when the IAQ level detected in below the threshold value or a different threshold value. According to yet another embodiment, the microcontroller can extrapolate an occupancy schedule according to the pattern of IAQ levels detected. According to another embodiment, the microcontroller can use the dataset with updated IAQ levels with timing data to update the pattern. The microcontroller can then update the occupancy schedule according to the updated pattern.

The method 200 further includes storing the IAQ levels with the timing data 250, particularly storing the IAQ level with the timing data in the memory of the IAQ sensor. The memory can hold a history of IAQ levels for further processing by the microcontroller. The history of IAQ levels can be stored in a history buffer of the memory. According to another embodiment, the microcontroller can process the history of IAQ levels by applying a smoothing function or a low path filter and determine an occupancy status. According to an embodiment, the occupancy status can be binary, i.e., occupied or unoccupied.

The method 200 further includes determining an occupancy schedule and subdividing the occupancy schedule into a plurality of periods 260. According to one embodiment, the IAQ sensor assumes the controlled space is utilized according to a repeating schedule of a week or a multiple of a week. For example, the IAQ sensor can fit the IAQ level data to a weekly schedule. According to another embodiment, the microcontroller determines a suitable repeating period for the occupancy schedule according to the IAQ level pattern recognized by the microcontroller.

The method 200 further includes determining an occupancy status for each of the plurality of periods according to the respective IAQ level 270. The occupancy status can be occupied or unoccupied. According to one embodiment, after detecting a predetermined number of IAQ levels during the powerup period, the microcontroller applies a smoothing function and/or a low path filter that determines the occupancy status of the controlled room based on the history of the IAQ levels stored in the history buffer. According to another embodiment, the microcontroller applies a smoothing function and/or a low path filter after detecting a predetermined period of time. A predetermined threshold value can be applied to determine the occupancy statues. The microcontroller determines the controlled space is occupied if the IAQ level is above the predetermined threshold value and is unoccupied if the IAQ level equals or is lower than the predetermined threshold value. According to another embodiment, the threshold value can be determined by the smoothing function or the low pass filter according to the history of IAQ levels. Accordingly, the occupancy status of each of the plurality of periods can be occupied or unoccupied as determined by the microcontroller according to the history of the IAQ levels. The IAQ level can be a $CO_2$ level, a VOC level, or the like.

The method 200 further includes detecting IAQ levels with the IAQ detector at an active interval during each of the periods in which the occupancy status is occupied 280. The method further includes detecting IAQ levels with the IAQ detector at an inactive interval during each of the periods in which the occupancy status is unoccupied 290. According to one embodiment, the IAQ level in a controlled space is primarily contributed by the occupants. When the controlled space is unoccupied, the IAQ level should maintain at a low level without significant changes over time. Accordingly, the IAQ detector can detect IAQ level at a longer interval and still accurately capture an accurate pattern of the IAQ level in the controlled space. When the controlled space is occupied, the IAQ level increases to a higher level and fluctuates proportionally to the number of occupants in the controlled space in given moment. Accordingly, when the controlled space is occupied, the IAQ detector should detect IAQ levels at a shorter interval to capture an accurate pattern of the IAQ level that reflects fluctuations. The microcontroller can set the sampling interval of the IAQ detector according to the occupancy status. The IAQ level can be a $CO_2$ level, a VOC level, or the like. The IAQ detector can be a $CO_2$ detector, a VOC detector, or the like.

In an embodiment, before establishing an occupancy schedule, the microcontroller operates the IAQ detector to detect IAQ level at a predetermined interval. According to an embodiment, the time period before establishing the occupancy schedule is a powerup period. The IAQ detector detects IAQ at the predetermined interval can monitor the IAQ levels in the controlled space and capture the fluctuations of IAQ levels in the controlled space. For example, the predetermined sampling interval can be 5 minutes. After the powerup period and an occupancy schedule is determined, the microcontroller switches the sampling interval to an active interval for time periods in the occupancy schedule with an occupied status. The microcontroller further switches the sampling interval to an inactive interval for time periods in the occupancy schedule with an unoccupied status. The active interval and the inactive interval can be predetermined values. For example, the active interval can be 2 minutes, and the inactive interval can be 15 minutes. The IAQ level can be a CO2 level, a VOC level, or the like. The IAQ detector can be a CO2 detector, a VOC detector, or the like.

The method of 200 further includes updating occupancy status by including IAQ levels detected after the powerup period 295. According to one embodiment, the occupancy status can be updated following a surprise reading. The surprise reading can be a IAQ level higher than a first predetermined value during a period with an unoccupied status. The inconsistent reading can be a IAQ level lower than a second predetermined value during a period with an occupied status. The IAQ level can be a CO2 level, a VOC level, or the like.

The microcontroller starts to update the occupancy schedules after the powerup period. According to an embodiment, the time period after the powerup period can be an enhancing period. During the enhancing period, the occupants of the controlled space can change their weekly schedule over time. An RTC can track real time or relative time. For example, when the IAQ sensor with the RTC tracking a relative time, the occupants of the controlled space may shift their schedules due to daylight savings. For another example, the occupants of a house may occupy the house according to one schedule during the school year and a different schedule during summer and winter breaks. During the enhancing period, the IAQ sensor can update the occupancy schedule when the IAQ level is inconsistent with the expected occupancy status. For example, during a time period on the occupancy schedule having an unoccupied status, the controlled space is expected to be unoccupied. A IAQ level above a predetermined level is inconsistent with the expected occupancy status. According to one embodiment, this inconsistent event can trigger the microcontroller to re-run the smoothing function or the low path filter. Accordingly, the re-run incorporates the more recent IAQ levels and updates the occupancy schedule accordingly. Similarly, during a time period when the controlled space is expected to be occupied, a IAQ level lower than a predetermined level can be inconsistent with the expected occupancy status. Accordingly, the microcontroller re-runs the smoothing function or the low path filter and updates the occupancy schedule. The IAQ level can be a CO2 level, a VOC level, or the like.

According to another embodiment, the IAQ sensor can be conservative in shortening the sampling interval and be biased towards over sampling. Over sampling is when the IAQ detectors take detection more frequently than needed to reliability capture a trend, a pattern, or a fluctuation of IAQ in the controlled space. Over sampling can maintain the reliability of the history of IAQ levels but consume more battery power. Under sampling is when the IAQ detectors take detection less frequently than needed to reliability capture a trend, a pattern, or a fluctuation of IAQ in the controlled space. Under sampling can save battery but risk missing fluctuations in the IAQ levels. The IAQ level can be a CO2 level, a VOC level, or the like.

The threshold for shortening the sampling interval can be triggered more rapidly by requiring only a smaller number of inconstant events. The threshold for lengthening the sampling interval can be triggered more conservatively by requiring a larger number of inconsistent events. For example, the microcontroller can reduce the sampling interval from the inactive interval to the active interval after a first predetermined number of inconsistent events.

In contrast, the microcontroller can increase the sampling interval from the active interval to the inactive interval after a second predetermined number of inconsistent events, wherein the second predetermined number is larger than the first inconsistent number. For example, the microcontroller can shorten the sampling interval to the active interval after only one inconsistent reading. For example, the microcontroller can lengthen the sampling interval to the inactive interval after five inconsistent readings.

By incorporating the RTC and generating an occupancy schedule that can be continuously updated, the sampling interval can be updated more synchronized with the occupant's actual occupancy schedule which may be evolving over time, and conserve battery life of the IAQ sensor.

According to another embodiment, the microcontroller can increase or decrease the sampling interval according to and soon after at least one IAQ levels detected. For example, the microcontroller can increase the sampling interval immediately after only one IAQ level detected that is above a threshold value. The microcontroller can reduce the sampling interval immediately after only one IAQ level detected that is below the threshold value, or a different threshold value. The threshold values can be predetermined or generated through a machine learning process using the IAQ levels detected for the controlled space over time. According to another embodiment, the microcontroller can increase the sampling interval after a consecutive number of or an average among a number of IAQ levels detected that is above a threshold value; and the microcontroller can decrease the sampling interval after a consecutive number of or an average among a number of IAQ levels detected that is below the threshold value, or another threshold value. By adjusting the sampling interval based on the IAQ level detected soon before the adjustment, the sampling interval adjustment is lagged behind the actual occupancy schedule of the occupants, but battery life of the IAQ sensor can still be conserved by the delayed reducing of sampling. Further, adjusting the sampling interval based on the IAQ level detected soon before the adjustment can be more suitable for a controlled space where the usage or the occupancy is more sporadic and is less predictable.

It is appreciated that the method of FIG. 3 can be accomplished by some and not all the processes in FIG. 3. The method 200 includes powering an IAQ sensor with a battery 210 and detecting IAQ levels 220. In an embodiment, one or more of 230, 240, 250, 260, 270, 280, 290, 295 in FIG. 3 are optional.

Aspects. It is noted that any of aspects 1-10 can be combined with any one of aspects 11-20.

Aspect 1. A method for extending battery life of an indoor air quality ("IAQ") sensor for a controlled space, comprising:
  powering, using a battery, the IAQ sensor having a IAQ detector, a radio, the battery, and a microcontroller with a memory and a processor;
  detecting, using the IAQ detector, an IAQ at a predetermined interval to provide a plurality of IAQ levels;
  storing the IAQ levels in the memory;
  transmitting, using the radio, the IAQ levels to a remote controller for a HVACR system serving the controlled space; and
  adjusting a sampling interval for the IAQ detector according to the IAQ levels detected.

Aspect 2. The method of aspect 1, wherein
  the IAQ detector is at least one of a $CO_2$ detector or a volatile organic compounds (VOC) detector, and
  the IAQ level is at least one of a $CO_2$ level or a VOC level.

Aspect 3. The method of any one of aspect 1-2, wherein
  the IAQ sensor further having a real time clock ("RTC") providing corresponding timing data for the IAQ levels, and
  the corresponding time data are stored with the IAQ levels in the memory.

Aspect 4. The method of any one of aspect 1-3, wherein adjusting the sampling interval for the IAQ detector by:
  determining an occupancy schedule for the controlled space based on the IAQ levels and the corresponding timing data, the occupancy schedule subdivided into a plurality of periods, wherein the determining the occupancy schedule includes determining an occupancy status for each of the plurality of periods based on the IAQ levels and the corresponding timing data from a plurality of occupancy statuses, the plurality of occupancy statuses including occupied and unoccupied;
  operating the IAQ detector according to the occupancy schedule such that:
    the IAQ detector detects the IAQ at an active interval during each of the plurality of periods in which the occupancy status is the occupied, and
    the IAQ detector detects the IAQ at an inactive interval during each of the plurality of periods in which the occupancy status is the unoccupied, the inactive interval being longer than the active interval; and
  transmitting, using the radio, at least one IAQ level detected by the IAQ detector operating according to the occupancy schedule.

Aspect 5. The method of any one of aspect 1-4, further comprising:
  changing the occupancy status of one of the plurality of periods from the unoccupied to the occupied when the IAQ level detected during the one of the plurality of periods is above a first threshold value over a first predetermined number of detections; and
  changing the occupancy status of one of the plurality of periods from the occupied to the unoccupied when the IAQ level detected during the one of the plurality of periods is below a second threshold value over a second predetermined number of sampling.

Aspect 6. The method of any one of aspect 1-5, wherein adjusting the sampling interval biased towards over sampling.

Aspect 7. The method of any one of aspect 1-6, wherein: adjusting the sampling interval biased towards over sampling by:
  setting the first predetermined number to be smaller than the second predetermined number, or
  setting the first predetermined number, the inactive interval, the second predetermined number times, and the active interval so that a first product of the first predetermined number times the inactive interval is smaller than a second product of the second predetermined number times the active interval.

Aspect 8. The method of any one of aspect 1-7, further comprising:
  detecting for the controlled space at least one of:
  a temperature level using a temperature detector, and a humidity level using a humidity detector; or
  transmitting the temperature level, or the humidity level using the radio.

Aspect 9. The method of any one of aspect 2-8, wherein at least one of the $CO_2$ detector, the VOC detector, the temperature detector, or the humidity detector is a modular unit plugged into the IAQ sensor and configured to be unplugged and removable from the IAQ sensor.

Aspect 10. The method of any one of aspect 4-9, wherein the occupancy schedule is determined using a machine learning algorithm included in the IAQ sensor, the occupancy status being determined by the machine learning algorithm, wherein the machine learning algorithm is configured to:
  read the IAQ levels and the corresponding timing data from the memory, and
  determine the occupancy status according to a pattern in the IAQ levels over time.

Aspect 11. An IAQ sensor that measures IAQ levels in a controlled space, comprising:
  a IAQ detector to detect IAQ at a sampling interval to provide a plurality of IAQ levels;
  a memory to store the IAQ level;
  a battery to power the IAQ sensor;

a microcontroller configured to adjust a sampling interval for the IAQ detector according to the IAQ levels detected; and a radio to transmit at least one IAQ level detected by the IAQ detector to a remote controller for a HVACR system serving the controlled space.

Aspect 12. The IAQ sensor of aspect 11, wherein the IAQ detector is at least one of a CO2 detector or a volatile organic compounds (VOC) detector, and the IAQ level is at least one of a CO2 level or a VOC level.

Aspect 13. The IAQ sensor of any one of aspects 11-12, wherein the IAQ sensor further having a real time clock ("RTC") providing corresponding timing data for the IAQ levels, and the corresponding time data are stored with the IAQ levels in the memory.

Aspect 14. The IAQ sensor of any one of aspects 11-13, wherein the microcontroller is further configured to adjust the sampling interval by:

determining an occupancy schedule for the controlled space based on the IAQ levels and the corresponding timing data, the occupancy schedule subdivided into a plurality of periods, wherein the determining the occupancy schedule includes determining an occupancy status for each of the plurality of periods based on the $CO_2$ levels and the corresponding timing data from a plurality of occupancy statuses, the plurality of occupancy statuses including occupied and unoccupied; and operating the IAQ detector according to the occupancy schedule such that:

the IAQ detector detects the IAQ at an active interval during each of the plurality of periods in which the occupancy status is the occupied, and the IAQ detector detects the IAQ at an inactive interval during each of the plurality of periods in which the occupancy status is the unoccupied, the inactive interval being longer than the active interval.

Aspect 15. The IAQ sensor of any one of aspects 11-14, wherein the microcontroller is further configured to adjust the sampling interval by:

changing the occupancy status of one of the plurality of periods from the unoccupied to the occupied when the $CO_2$ level detected during the one of the plurality of periods is above a first threshold value over a first predetermined number of detections; and changing the occupancy status of one of the plurality of periods from the occupied to the unoccupied when the $CO_2$ level detected during the one of the plurality of periods is below a second threshold value over a second predetermined number of sampling.

Aspect 16. The IAQ sensor of any one of aspects 11-15, wherein the microcontroller is further configured to change the occupancy biased towards over sampling.

Aspect 17. The IAQ sensor of any one of aspects 11-16, wherein the microcontroller is further configured to change the occupancy biased towards over sampling by:

setting the first predetermined number to be smaller than the second predetermined number, or setting the first predetermined number, the inactive interval, the second predetermined number times, and the active interval so that a first product of the first predetermined number times the inactive interval is smaller than a second product of the second predetermined number times the active interval.

Aspect 18. The IAQ sensor of any one of aspects 11-17, wherein the IAQ detector further includes at least one of a temperature detector to detect a plurality of temperature levels, and/or a humidity detector to detect a plurality of humidity levels in the controlled space; and the radio to transmit at least one of the temperature levels, and/or at least one of the humidity levels to the remote controller for the HVACR system serving the controlled space.

Aspect 19. The IAQ sensor of any one of aspects 12-18, wherein at least one of the $CO_2$ detector, the VOC detector, the temperature detector, or the humidity detector is a modular unit that can be plugged into the IAQ sensor and configured to be unplugged and removable from the IAQ sensor.

Aspect 20. The IAQ sensor of any one of aspects 14-19, wherein the occupancy schedule is determined using a machine learning algorithm included in the IAQ sensor, the occupancy status being determined by the machine learning algorithm, wherein the machine learning algorithm is configured to:

read the IAQ levels and the corresponding timing data from the memory, and determine the occupancy status according to a pattern in the IAQ levels over time.

The terminology used in this Specification is intended to describe particular embodiments and is not intended to be limiting. The terms "a," "an," and "the" include the plural forms as well, unless clearly indicated otherwise. The terms "comprises" and/or "comprising," when used in this Specification, specify the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts without departing from the scope of the present disclosure. This Specification and the embodiments described are exemplary only, with the true scope and spirit of the disclosure being indicated by the claims that follow.

What is claimed is:

1. A method for extending battery life of an indoor air quality ("IAQ") sensor for a controlled space, comprising:

powering, using a battery, the IAQ sensor having at least one IAQ detector, a radio, the battery, and a microcontroller with a memory and a processor, the at least one IAQ detector including one or more of a $CO_2$ detector and a volatile organic compounds ("VOC") detector;

detecting, using the at least one IAQ detector, an IAQ at a predetermined interval to provide a plurality of IAQ levels, the plurality of IAQ levels including one or more of $CO_2$ levels and VOC levels detected using the one or more of the $CO_2$ detector and the VOC detector;

storing the IAQ levels in the memory;
transmitting, using the radio, the IAQ levels to a remote controller for a HVACR system serving the controlled space;
determining an occupancy of the controlled space based on one or more of the $CO_2$ levels detected and the VOC levels detected; and
adjusting a sampling interval for the at least one IAQ detector according to the determined occupancy of the controlled space, the sampling interval being a rate between detections by the at least one IAQ detector.

2. The method of claim 1, wherein
the IAQ levels are one or more of the $CO_2$ levels and the VOC levels.

3. The method of claim 1, wherein
the IAQ sensor including a real time clock ("RTC") providing corresponding timing data for the IAQ levels,
the corresponding timing data is stored with the IAQ levels in the memory, and
the occupancy of the controlled space is determined based on the one or more of the $CO_2$ levels detected and the VOC levels detected and the corresponding timing data.

4. The method of claim 1, wherein
the determining of the occupancy includes determining an occupancy schedule for the controlled space, the determined occupancy schedule is subdivided into a plurality of periods, wherein the determining of the occupancy schedule includes determining an occupancy status for each of the plurality of periods from a plurality of occupancy statuses based on the one or more of the $CO_2$ levels and the VOC levels and corresponding timing data, the plurality of occupancy statuses including occupied and unoccupied,
adjusting the sampling interval for the at least one IAQ detector is by:
adjusting the at least one IAQ detector according to the determined occupancy schedule such that:
the at least one IAQ detector detects the IAQ at an active interval during each of the plurality of periods in which the occupancy status is the occupied, and
the at least one IAQ detector detects the IAQ at an inactive interval during each of the plurality of periods in which the occupancy status is the unoccupied, the inactive interval being longer than the active interval, and
transmitting, using the radio, the IAQ levels detected by the at least one IAQ detector operating according to the determined occupancy schedule.

5. The method of claim 4, further comprising:
changing the occupancy status of a first one of the plurality of periods from the unoccupied to the occupied when one of the IAQ levels detected during the first one of the plurality of periods is above a first threshold value over a first predetermined number of detections; and
changing the occupancy status of a second one of the plurality of periods from the occupied to the unoccupied when one of the IAQ levels detected during the second one of the plurality of periods is below a second threshold value over a second predetermined number of detections.

6. The method of claim 5, wherein:
the adjusting the sampling interval is biased towards over sampling by:

setting the first predetermined number to be smaller than the second predetermined number, or
setting the first predetermined number, the inactive interval, the second predetermined number, and the active interval so that a first product of the first predetermined number times the inactive interval is smaller than a second product of the second predetermined number times the active interval.

7. The method of claim 1, wherein
the adjusting the sampling interval is biased towards over sampling.

8. The method of claim 1, further comprising:
detecting for the controlled space at least one of:
a temperature level using a temperature detector, or
a humidity level using a humidity detector; and
transmitting at least one of the temperature level detected or the humidity level detected using the radio,
wherein at least one of the $CO_2$ detector, the VOC detector, the temperature detector, or the humidity detector is a modular unit plugged into the IAQ sensor and is configured to be unplugged and removable from the IAQ sensor.

9. The method of claim 1, wherein
the occupancy is determined using a machine learning algorithm included in the IAQ sensor, the occupancy being determined by the machine learning algorithm, wherein the machine learning algorithm is configured to:
read the IAQ levels and corresponding timing data from the memory, and
determine the occupancy according to a pattern in the IAQ levels over time.

10. An IAQ sensor that measures IAQ levels in a controlled space, comprising:
at least one IAQ detector to detect an IAQ at a predetermined interval to provide a plurality of IAQ levels, the at least one IAQ detector including one or more of a $CO_2$ detector and a volatile organic compounds ("VOC") detector, and the plurality of IAQ levels including one or more of $CO_2$ levels and VOC levels detected using the one or more of the $CO_2$ detector and the VOC detector;
a memory to store the IAQ levels;
a battery to power the IAQ sensor;
a radio to transmit the IAQ levels detected by the at least one IAQ detector to a remote controller for a HVACR system serving the controlled space;
a microcontroller configured to:
determine an occupancy of the controlled space based on the IAQ levels one or more of the $CO_2$ levels detected and the VOC levels detected, and
adjust a sampling interval for the at least one IAQ detector according to the determined occupancy of the controlled space, the sampling interval being a rate between detections by the at least one IAQ detector, wherein the adjusting of the sampling interval extends battery life of the IAQ sensor.

11. The IAQ sensor of claim 10, wherein
the IAQ levels are one or more of the $CO_2$ levels and the VOC levels.

12. The IAQ sensor of claim 10, further comprising:
a real time clock ("RTC") providing corresponding timing data for the IAQ levels,
wherein the corresponding timing data is stored with the IAQ levels in the memory, and the occupancy of the controlled space is determined based on one or more of the $CO_2$ levels detected and the VOC levels detected and the corresponding timing data.

13. The IAQ sensor of claim 10, wherein
the microcontroller is configured to determine the occupancy of the controlled space includes the microcontroller being configured to determine an occupancy schedule for the controlled space, the occupancy schedule is subdivided into a plurality of periods, wherein the determining of the occupancy schedule includes determining an occupancy status for each of the plurality of periods from a plurality of occupancy statuses based on the one or more of the $CO_2$ levels and the VOC levels and corresponding timing data, the plurality of occupancy statuses including occupied and unoccupied, and
wherein the microcontroller is further configured to adjust the sampling interval by:
adjusting the at least one IAQ detector according to the determined occupancy schedule such that:
the at least one IAQ detector detects the IAQ at an active interval during each of the plurality of periods in which the occupancy status is the occupied, and
the at least one IAQ detector detects the IAQ at an inactive interval during each of the plurality of periods in which the occupancy status is the unoccupied, the inactive interval being longer than the active interval.

14. The IAQ sensor of claim 13, wherein
the microcontroller is further configured to adjust the sampling interval by:
changing the occupancy status of a first one of the plurality of periods from the unoccupied to the occupied when one of the IAQ levels detected during the first one of the plurality of periods is above a first threshold value over a first predetermined number of detections; and
changing the occupancy status of a second one of the plurality of periods from the occupied to the unoccupied when one of the IAQ levels detected during the second one of the plurality of periods is below a second threshold value over a second predetermined number of detections.

15. The IAQ sensor of claim 14, wherein
the microcontroller is further configured to change the sampling interval biased towards over sampling by:
setting the first predetermined number to be smaller than the second predetermined number, or
setting the first predetermined number, the inactive interval, the second predetermined number, and the active interval so that a first product of the first predetermined number times the inactive interval is smaller than a second product of the second predetermined number times the active interval.

16. The IAQ sensor of claim 10, wherein
the microcontroller is further configured to change the sampling interval biased towards over sampling.

17. The IAQ sensor of claim 10, further comprising:
at least one of a temperature detector to detect a plurality of temperature levels or a humidity detector to detect a plurality of humidity levels in the controlled space,
wherein the radio is configured to transmit at least one of the temperature levels detected or at least one of the humidity levels detected to the remote controller for the HVACR system serving the controlled space.

18. The IAQ sensor of claim 17, wherein
at least one of the $CO_2$ detector, the VOC detector, the temperature detector, or the humidity detector is a modular unit that can be plugged into the IAQ sensor and is configured to be unplugged and removable from the IAQ sensor.

19. The IAQ sensor of claim 10, wherein
the occupancy is determined using a machine learning algorithm included in the IAQ sensor, the occupancy being determined by the machine learning algorithm, wherein the machine learning algorithm is configured to:
read the IAQ levels and corresponding timing data from the memory, and
determine the occupancy according to a pattern in the IAQ levels over time.

20. The IAQ sensor of claim 10, further comprising:
a passive infrared ("PIR") sensor, wherein the occupancy of the controlled space is determined based on one or more of the $CO_2$ levels detected and the VOC levels detected and sensing by the PIR sensor.

* * * * *